United States Patent [19]

Harwood et al.

[11] Patent Number: 5,026,709
[45] Date of Patent: Jun. 25, 1991

[54] METHOD FOR THE PREPARATION OF A THEOPHYLLINE SUSTAINED RELEASE PHARMACEUTICAL COMPOSITION AND THE COMPOSITION PREPARED THEREBY

[75] Inventors: Richard J. Harwood, Bensalem; Gunvant N. Mehta, Lansdale; Ramesh C. Jhawar, Yardley; Liang-Lii Huang, Maple Glen; Wayne M. Grim, Doylestown; Shun P. Li, Upper Darby, all of Pa.

[73] Assignee: Rorer Pharmaceutical Corporation, Fort Washington, Pa.

[21] Appl. No.: 203,435

[22] Filed: Jun. 7, 1988

Related U.S. Application Data

[63] Continuation of Ser. No. 848,991, Apr. 7, 1986, abandoned.

[51] Int. Cl.$^5$ ............... A01N 43/90; A01K 31/52
[52] U.S. Cl. ................... 514/263; 424/468; 424/480; 514/826
[58] Field of Search ............... 514/826, 263; 424/482, 424/480, 468

[56] References Cited

U.S. PATENT DOCUMENTS

| | | | |
|---|---|---|---|
| 3,109,775 | 11/1963 | Shepard | 424/422 |
| 4,587,118 | 5/1986 | Hsiao | 424/494 |
| 4,588,366 | 5/1986 | Glatt | 425/422 |
| 4,663,150 | 5/1987 | Panoz et al. | 424/494 |

FOREIGN PATENT DOCUMENTS

8300284 2/1983 Int'l Pat. Institute .

*Primary Examiner*—Joseph L. Schofer
*Assistant Examiner*—Peter F. Kulkosky
*Attorney, Agent, or Firm*—Martin F. Savitzky; James A. Nicholson; Alexis Barron

[57] ABSTRACT

A method for the preparation of a sustained release pharmaceutical composition comprising forming a fluidized ring of said particles and contacting said particles maintained suspended in said ring with a liquid composition containing a pharmaceutically active material and an alkali-soluble material.

24 Claims, 1 Drawing Sheet

METHOD FOR THE PREPARATION OF A THEOPHYLLINE SUSTAINED RELEASE PHARMACEUTICAL COMPOSITION AND THE COMPOSITION PREPARED THEREBY

This is a continuation of co-pending application Ser. No. 848,991, filed on Apr. 7, 1986, now abandoned.

FIELD OF THE INVENTION

This invention relates to a pharmaceutical composition of the type which is effective in releasing into the body biologically active material(s) over a prolonged period of time, and to a process for the preparation of said type of composition. A particular aspect of the present invention relates to a process for the preparation of a composition which is effective in releasing theophylline or a derivative thereof into the body over a prolonged period of time.

Theophylline and derivatives thereof are known biologically active materials which are used, for example, as bronchodilators. It has long been recognized that theophylline tends to cause problems when administered in orally neat form. Gastrointestinal, CNS and cardiovascular side effects due to excessive blood concentrations are not uncommon. To avoid or deter the aforementioned-type problems, efforts have been made to administer theophylline in an enteric and controlled release form, that is, a form in which a predetermined dose of theophylline is provided with an enteric matrix and coating which enables it to release theophylline into the stomach and to pass into the intestine where the theophylline is released at a controlled rate over a relatively long period of time, for example, over a 6- to 12-hour period.

REPORTED DEVELOPMENTS

Various forms of enteric-coated and sustained release medicaments, including theophylline, are described in U.S. Pat. Nos. 3,109,775; 4,083,949; and 4,261,970; and in PCT application bearing Publication No. WO 83/00284. Speaking generally, the aforementioned patents disclose a pharmacologically-active material encased in a slowly dissolvable coating or in a porous material which is insoluble in the acid environment of the stomach and which allows the active material to pass therethrough and into the intestine. For example, a typical sustained-release preparation comprises an inert core, such as a sugar grain, coated with an adhesive which has applied thereto a pharmacologically active substance. The amount of active substance may be built up by forming layer upon layer of the adhesive coating and active substance. Once the desired amount of active substance has been applied, the multi-layered structure is covered with a permeable membrane which resists dissolution and otherwise being degraded in the stomach and in the intestine and which allows the desired pharmaceutical substance, for example, theophylline to pass through the pores thereof as it is dissolved by the liquid solvent of the intestine.

One problem encountered with theophylline preparations is that relatively high concentrations of theophylline, which is highly soluble in the acidic environment of the stomach, pass into the stomach where the theophylline can cause local and systemic side effects following absorption. Aforementioned U.S. Pat. No. 4,083,949 discloses a membrane which is prepared from a liquid mixture of membrane-forming material and an acid insoluble, alkali soluble material. Such a membrane is said to substantially prevent the premature release of theophylline in the acidic environment of the stomach. However, the use of such a membrane can result in an undue rapid release of theophylline in the intestine. This type of problem has been addressed by the preparation and the use of sustained release compositions, which have been prepared by numerous methods.

Sustained release compositions are generally prepared by the use of successive coatings of different materials which provide for a gradual release of a pharmacologically active material by the peeling away of successive layers of materials, each of which has been painstakingly applied. The coating methods which result in such a composition may be effected in a rotating coating pan commonly used for the manufacture of sugar-coated pills. In one prior art process involving the use of a coating pan, a sustained release theophylline preparation is prepared by applying to a batch of seed particles an alkali soluble adhesive in liquid form, followed by the addition of finely divided particles of solid theophylline. More specifically, the method involved:

(A) forming on a seed a wet layer of an alkali soluble adhesive material followed by contacting the wet seed particles with theophylline in finely divided form;

(B) drying the wet layer including theophylline;

(C) forming on said dried layer one or more additional layers of an alkali soluble adhesive material followed by contacting thereto theophylline in finely divided form, each of said layer or layers being formed initially in wet form and drying said wet layer or each of said wet layers prior to the application thereto of any overlying material;

(D) covering said multi-layered core with a membrane, capable of forming pores and comprising (1) an acid insoluble and alkali insoluble material and (2) a water soluble material; and (E) depositing on said membrane a non-enteric coating comprising (1) an acid insoluble and alkali soluble material and (2) an acid insoluble and alkali insoluble material.

Although the theophylline-containing composition prepared by the pan coating technique exhibits many of the properties desired in a sustained release preparation, the pan coating process involved more than about two dozen repeated and time consuming layering and drying steps.

Fluidized bed and column techniques have also been used to prepare sustained release compositions. In these techniques, seed particles are suspended by a stream of air and coated by the addition of adhesives and powdered ingredients, and also involve numerous layering steps which are time consuming and cost ineffective. In PCT publication no. WO/83/00284, a Glatt column air suspension system is used to apply to suspended seed particles multi-layers of a liquid suspension of theophylline and polyvinylpyrrolidone and isopropanol. The multi-layered product is then coated with a mixture of cellulose materials. It has been reported that the product believed to be prepared according to the aforementioned process exhibits an inhibited release pattern when administered concurrently with or shortly after the ingestion of food.

It is an object of the present invention to provide a method for the preparation of a sustained release composition which is relatively simple and involves a minimum number of coating steps, and which provides for a composition characterized by optimum time delayed release characteristics independent of a patient's dietary behavior.

SUMMARY OF THE INVENTION

In accordance with this invention, there is provided a process for the preparation of a sustained release pharmaceutical composition, including a seed particle coated with a pharmacologically active compound-containing layer, comprising (A) forming a fluidized ring of said seed particles by subjecting simultaneously said particles to a centrifugal force, a perpendicular gravitational force, and a circumferential positive fluid pressure force substantially opposed to said gravitational force; and (B) contacting said particles while they are maintained suspended in said ring with a liquid composition containing said pharmacologically active compound and an alkali soluble material and for a period of time sufficient to coat said particles.

Another aspect of the present invention relates to a sustained release composition, which under the influence of gastrointestinal juices releases a pharmacologically active ingredient at a desired rate, and which comprises a seed core, a single layer including said pharmacologically active ingredient, and an encapsulating coating capable of forming pores. A particularly preferred aspect of the composition of the present invention relates to the relatively invariant release characteristics thereof under fasting and/or meal ingestion conditions.

Still another aspect of the present invention relates to a method for the treatment of physiological disorders, for example, bronchial disorders such as asthma, comprising the oral ingestion by an individual of a pharmaceutical composition, as described above, wherein said preparation may be administered at prescribed intervals independent of the presence or absence of food in said individual's digestive tract.

DETAILED DESCRIPTION OF THE INVENTION

Figure 1:
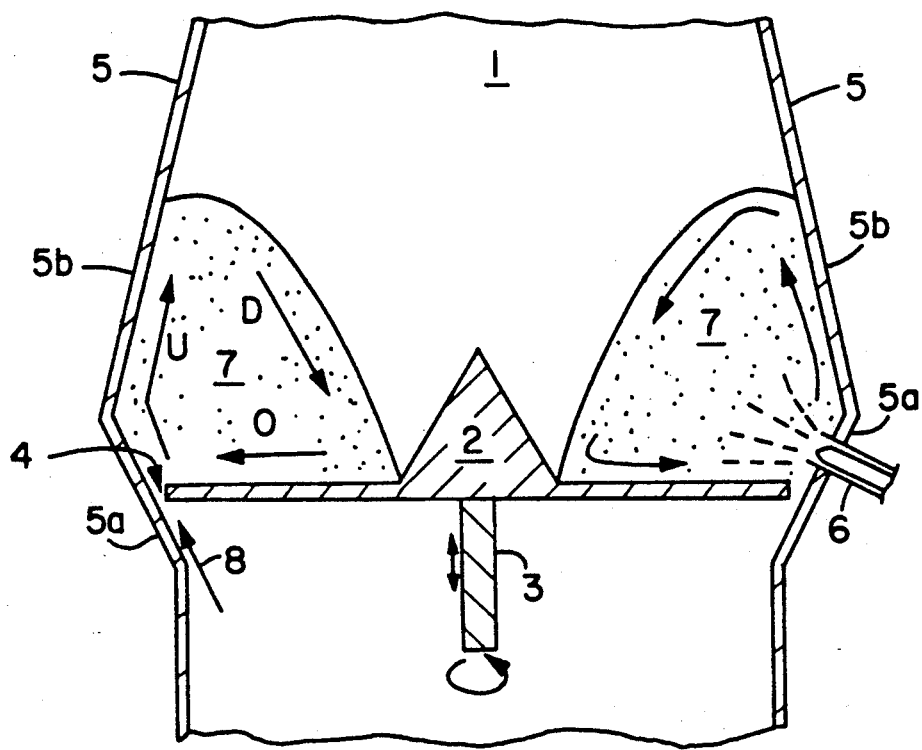
FIG. 1 is a partial sectional side elevational view of a circular mixing and granulating device showing a particle fluidizing and coating process in accordance with the present invention.

Unless indicated otherwise, the following terms as used herein are understood to have the definitions indicated below.

"Alkali soluble material" means a material which is soluble in the alkaline conditions of the intestine and of the type suitable for use in forming a sustained release pharmaceutical and which is capable of functioning as a binder to agglomerate particles of a pharmacologically active compound in forming a coating of the sustained release composition of the present invention.

"Enteric coating" means a coating which permits a medicament to pass through the stomach substantially without being released in the stomach fluids.

"Membrane" means a semipermeable structure permitting the passage therethrough of water and other like sized molecules.

"Non-enteric coating" means a coating which permits the release of a medicament in the stomach and which may be a continuous, discontinuous, irregular or spotty coating.

"Pore" means an opening which permits the passage therethrough of molecules of a size larger than water.

"Seed" is a small particle of material of the type that is suitable for use in sustained release pharmaceutical compositions, and have a mean particle size of about 600 to about 850 microns. An example of such a material is a combination of suga and cornstarch.

"Theophylline" means theophylline and derivatives thereof which are effective bronchodilators for the relief of asthma, including, for example, guaithylline (3,7-Dihydro-1,3-dimethyl-1H-purine-2,6-dione compounded (1:1) with 3-(2-methoxyphenoxy)-1,2-propanediol).

In accordance with the present invention, a desired amount of seed particles 7 is introduced into the chamber 1 of the mixing and coating device shown in FIG. 1 while the rotor disc 2 rotates about the shaft 3 and a positive fluid pressure, shown as arrow 8, is applied through clearance 4. The fluid comprises preferably an inert gas, such as air, nitrogen or carbon dioxide and emanates from a source not shown in FIG. 1. The rotating rotor disc 2 imparts a centrifugal force to the seed particles 7 propelling them towards the chamber wall 5, where the pressure of the upwardly moving fluid, shown as arrow 8, imparts to the particles 7 upward movement in substantial opposition to the force of gravity. The chamber wall 5 of the embodiment of the device shown in FIG. 1 comprises an outwardly inclined portion 5a and an inwardly inclined portion 5b. The outwardly inclined portion 5a can function together with the raising and lowering the rotor disc 2 so as to control the fluid volume passing through clearance 4, while the inwardly inclined portion 5b functions to deflect the upwardly moving particles 7 toward the central portion of the chamber 1. The particles 7 rise in the chamber 1 until the force of gravity overcomes the decreasing force of the fluid pressure. The particles 7 then fall towards the central portions of the rotor disc 2. The motion of the seed particles 7 is depicted in two dimensions in FIG. 1 by lines U, D and O, and the resulting shape and motion of the seed particles 7 is referred to throughout this application as a "fluidized ring". Of course, the particles 7 are not confined to two dimensions but also rotate about within the volume of the fluidized ring as a result of the rotation of the disc.

In the present process, a liquid coating composition including the pharmacologically active material and alkali soluble material is introduced into the chamber 1 by suitable means such as one or more spraying nozzles. The liquid coating composition is thereby contacted with the seed particles 7 as the particles rotate about the chamber and pass through the space where the coating composition is introduced into the ring. The preferred method of coating the seed particles 7 comprises the spraying of a fine spray mixture of air and the atomized liquid coating composition through the nozzle 6, and the coating of the particles occurs initially as the particles pass within the volume of sprayed coating composition emanating from the inlet nozzle 6.

In order to facilitate the spraying operation, the liquid coating composition includes a diluent such as a lower alkyl alcohol or low boiling haloalkyl solvent, with preferred diluents being ethanol, isopropanol and methylene chloride and mixtures thereof. Additionally, water may be included in the coating composition for the purpose of controlling the amount of static electricity generated during the coating process and in quantities effective for this purpose. It has been determined that the effective anti-static amounts of water can be used in the coating compositions without adversely affecting the dissolution rate of the sustained release composition. The rate of spraying into the fluidized ring should be sufficient to uniformly distribute the coating composition throughout the fluidized ring of seed particles and is dependent on the number of spray nozzles used in the process, the amount of the seed particles contained in the fluidized ring as well as the form of, the viscosity of and the nature of the coating composition. Typical spraying rates range from about 50 to about 700 g/min/nozzle.

In a particularly preferred embodiment of the present process, the coating composition comprises a suspension of solid particles of pharmacologically active material in a liquid dispersant comprising a lower alkyl alcohol. The suspension also includes the alkali soluble material in either liquid or solid form. The lower alkyl alcohol facilitates the admixture of the suspension with the fluidized ring of seed particles 7 as well as the clog-free spraying of the suspension. The lower alkyl alcohol may be ethanol(denatured and/or 200 proof), isopropanol, n-propanol or a mixture of both.

The size of the solid particles of pharmacologically active material has a measurable effect on the sustained release properties of the final product. It is preferred, in order to optimize the release rate of the pharmacologically active material, that the size of the solid particles of pharmacologically active material be "micronized", that is on the order of less than about one to about 50 microns, or a size measured on the order of about 300 mesh or more, based on the micromeroGragh system of measurement.

It is advantageous that the suspension include a percentage amount of solid pharmacologically active particles that will facilitate and promote the spraying of the suspension into the fluidized ring. It is believed that an effective amount of solid particles in the suspension can be from about 30 g to about 60 g per 100 g of suspension and is preferably about 40 g to about 55 per 100 g of suspension. It is also advantageous to coat the seed particles with an amount of pharmacologically active particles that will form a complete and continuous coating of agglomerated particles on the surface thereof. It should be understood that the total amount of the pharmacologically active particles in the sustained release composition should be sufficient to provide a source of active material throughout the desired sustained release period. Although there are many variables involved in the formulation and present process which can effect the release rate of the pharmacologically active material in the sustained release composition, the composition can comprise from about 40 to about 90 wt. % and preferably about 50 to about 65 wt. % of such active material based on the total dried weight of the composition.

The rotational rate of the rotor shaft 3 and the positive fluid pressure 8 are controlled in order to provide the appropriate conditions for the creation of a "fluidized ring" of solid particles 7 and for the layering of coating materials onto the seed particles in a uniform manner. Typical rotor speeds range from about 100 to about 300 rpm and are preferably within the range of about 120 to about 200 rpm and may vary within these ranges during the course of the coating process. The fluid pressure depends on the amount of material introduced into the chamber 1 and can range from about 30 to about 60 psi.

The temperature of chamber 1 and of the inert gas passing through the clearance 4 are controlled throughout the coating process. To effect this control, the fluidized ring and the inert gas are heated and maintained at a temperature within a range sufficient to volatilize the diluent contained in the coating compositions at a rate which permits the uniform coating of the seed particles. It is believed that in most applications, an effective temperature for the inert gas is about 30° to about 75° C., and preferably at about 35° to about 50° C., while an effective temperature for the fluidized ring is about 20° to about 45° C. and preferably about 25° to about 35° C.

Exemplary equipment which can be used in the present process include the Rotor Granulators sold by Glatt Air Techniques, Inc. and the Vector/Freund Spir-a-Flow sold by Vector Corporation. The Spir-a-Flow equipment introduces into the coating process an additional force which is derived from air pressure passing through numerous perforations in the inner portion of the rotor disc. This additional force creates eddies and currents in the inner volume of the fluidized ring and serve to increase the rate and improve the efficiency of the coating operation.

For certain applications, it is advantageous to provide an additional coating overlaying the coated seed particles 7. This additional coating comprises a porous membrane having pores of a size sufficient to permit a pharmacologically active compound such as theophylline to pass therethrough, may be formed by (C) charging a fluidized ring containing said coated seed particles prepared by step (B) above with a porous membrane-forming solution comprising a mixture of an alkali insoluble and acid insoluble component and a water soluble component. Preferably, the mixture from which the porous membrane is formed comprises an acid insoluble and alkali insoluble material not otherwise degradable in the environments of both the stomach and intestine and a water soluble material which in the aqueous environment of the stomach and intestine dissolves to form pores in the membrane. In preferred form, the ratio of membrane-forming material to water soluble material in the membrane and membrane-forming solution is about 5:1 to about 20:1, and more preferably about 8:1 to about 15:1. Exemplary of such porous membrane-forming solutions are those comprising about 5 to about 10 g, and preferably about 6 to about 8 g of acid insoluble, alkali insoluble material per 100 g of coating solution, and about 0.5 to about 1 g and preferably about 0.6 to about 0.8 g of water soluble material per 100 g of coating solution. The amount of membrane-forming material combined with the particles coated in step (B) above may range from about 0.1 to about 2%, and preferably about 0.3 to about 1.3% of the total dried weight of the composition.

In most applications, a uniform membrane is desireable. It is believed that such a membrane provides for a reproducible and controlled rate of dissolution of the underlying pharmacologically active material. It has been determined that the use of dilute membrane-forming solutions result in more uniform membranes than more concentrated solutions. It has also been found that those compositions having more uniform membranes and containing less membrane-forming material possess desired sustained release properties while compositions having less uniform membranes require more membrane-forming material to exhibit similarly desired release properties. Accordingly, for many applications of the present invention, the use of a less concentrated porous membrane-forming solution can reduce the total amount of membrane-forming material incorporated into the present sustained release composition to obtain its desirable sustained release properties.

In general, and as will be described in detail below, the membrane can be formed by combining the coated seed particles with a liquid solution comprising a solvent which has dissolved therein said mixture of materials. Exemplary solvents include lower alkyl alcohols such as ethanol(denatured and 200 proof), isopropanol or n-propanol or haloalkyls such as methylene chloride or carbon tetrachloride. A solid pore-forming membrane is formed from the solution as the solvent evaporates.

It is preferred to use as the acid insoluble and alkali insoluble membrane-forming material a cellulose ether, most preferably a lower alkyl cellulose ether, for example, ethyl cellulose. For the water soluble material it is preferred to use a lower alkylene glycol, for example, propylene glycol. In a highly preferred form, the porous membrane of the resulting sustained release composition comprises ethyl cellulose and propylene glycol. The following solution can be used to good advantage, the amounts of ingredients being based on 100 g of solution.

| Ingredients | Amount per 100 g |
|---|---|
| ethyl cellulose 10 cps | 7 g |
| propylene glycol | 0.8 g |
| denatured ethanol | qs |

The porous membrane-forming solution is applied to the coated seed particles by spraying the solution into a fluidized ring comprising seed particles coated in step (B) above. The rate of spraying may differ from that used for the coating of step (B) due to the differences between the two liquid spray formulations including the amounts of materials in the respective liquid compositions as well as the differences in the desired thickness of each layer or coating. The rate may also vary as a function of the size of the batch of material being processed in the chamber. In the preferred applications, the membrane-forming solution is applied at a rate which can range from about 20 to about 1000 g/min/per nozzle, and in most preferred applications at a rate of about 20 to about 500 g/min/per nozzle.

Upon the completion of each coating operation, the motion of the fluidized ring of coated particles is maintained and heating is continued in order to dry the coated particles and remove volatile diluents included in the spraying compositions. The complete drying of the coated particles may be accomplished as an operation contiguous with the coating operation conducted in the chamber 1, but certain considerations including the nature of the diluent, the desired thickness of the coating and the mechanical limitations on the mixing apparatus may require a separate drying operation. For the applications where these considerations prevail, the partially dried coated particles are removed from the chamber 1 and their drying is completed in a separate drying device such as a hot air oven or the like.

A special embodiment of the present invention comprises a composition having an outermost coating which permits the aqueous contents of the stomach to penetrate therethrough and dissolve from the underlying membrane an amount of water soluble material which is less than that comprising the membrane. The non-enteric coating may exist either in the form of a discontinuous, irregular, or spotty film, covering only a portion of the surface of the membrane, or in the form of a thin continuous film having a minimum of structural integrity. Thus, in the acid environment of the stomach, the pharmacologically active ingredient, such as theophylline, is released only in small amounts, the major portion thereof being retained within the spherule.

The outermost, and preferably non-enteric, coating can be formed from a mixture of materials, one of which is both acid insoluble and alkali insoluble and not otherwise degradable in the environments of both the stomach and intestine. The other material of the mixture is alkali soluble, but acid insoluble. Typically, the coating is formed by dissolving the solid materials in a suitable solvent(s) and applying the resulting solution by spraying to the membrane-covered particles. As the solvent evaporates, a coating comprising a matrix of each of the materials is formed, with the alkali soluble, acid insoluble material also on the membrane thereby protecting to a limited extent the water soluble component of the membrane from dissolution in the aqueous environment of the stomach. It is preferred that the acid insoluble, alkali insoluble material of the coating comprise a cellulose ether, most preferably ethyl cellulose. It is preferred that the acid insoluble and alkali soluble material of the coating comprise shellac, cellulose acetate phthalate, methacrylic acid and methacrylic acid ester copolymer, with shellac as pharmaceutical glaze being most preferred.

It is also preferred that the ratio of acid insoluble, alkali insoluble material to acid insoluble, alkali soluble material be about 0.1:1 to about 1:1. Exemplary non-enteric coating solutions contain about 0.05 to about 0.5 g, and preferably about 0.08 to about 0.3 g of acid insoluble, alkali insoluble material per 100 g of coating solution, and about 0.05 to about 0.8 g and preferably about 0.1 to about 0.4 g of acid insoluble and alkali soluble material per 100 g of coating solution. The weight percent of the materials deposited by this coating solution based on the total weight of the coated particle can range, for example, from about 0.05 to about 0.7% w/w. Two exemplary formulations for the non-enteric coating solution are described by the following formulations where the amounts of ingredients are given per 100 gram of solution.

| Ingredients | Formulation 1 Amount per 100 g | Formulation 2 Amount per 100 g |
|---|---|---|
| ethyl cellulose 10 cps | 0.1 g | 2.4 g |
| pharmaceutical glaze | 0.6 g | 13.8 g |
| (total shellac solids) | (0.2 g) | (4.8 g) |
| denatured ethanol | 0.6 g | q.s. |
| methylene chloride | q.s. | — |

Another special embodiment of the present invention relates to the process and composition wherein the seed particle comprising the core of the sustained release composition also comprises a pharmaceutically active material. In many applications of the present invention, the use of a particle of pharmaceutically active material having a mean particle size of about 600 to about 850 microns as the seed particle may provide a convenient higher dosage form of the present composition. For example, about 10 to about 100% more of pharmaceutically active material may be included in a standard volume of sustained release pellets prepared using pharmaceutically active seed material. Such compositions may be described as "higher assay" sustained release compositions.

It is believed that the present invention will find particularly wide use in the preparation of a sustained release composition comprising theophylline as a pharmacologically active ingredient therein. The following examples describe a method for preparing theophylline sustained-release pharmaceutical compositions in accordance with the present invention.

EXAMPLE 1

A preferred theophylline-containing composition is prepared utilizing the following ingredients in the amounts indicated below.

| Ingredient | Amount per 100 g |
| --- | --- |
| theophylline USP (micronized anhydrous powder) | 60 g |
| non-pareil seeds (25/30 mesh fraction) | 24 g |
| pharmaceutical glaze (four pound cut) | 46 g |
| (total shellac solids content) | (16 g) |
| ethyl cellulose 10 cps | 0.4 g |
| propylene glycol USP | 0.04 g |
| denatured ethanol | qs |

The micronized theophylline anhydrous powder is dispersed in about 40 g of pharmaceutical glaze and about 37 g of denatured ethanol in a mixer or homogenizer. A Glatt Rotor Granulator (Model RGR-5) fitted with a Glatt GPCG 5/9 coating device and having parts like those shown in the apparatus of FIG. 1 is used to coat the non-pareil seeds, which are charged into the chamber 1. The rotor speed is set and maintained at 150 rpm, the air pressure is set at 1,100 m³ per hour, the temperature of the inlet air volume is set at about 40° C., and the fluidized ring temperature is set at about 30° C. The slurry of theophylline is sprayed into the fluidized ring through two nozzles at a rate, which varies within the range of about 50 to about 500 g/min., but which averages at about 200 g per minute. About 5 g of pharmaceutical glaze, containing 35% shellac solids, and about 4 g of denatured alcohol are added to the last 10% of the slurry prior to spraying into the fluidized ring. After all of the slurry is sprayed, rotation is continued and the theophyllineshellac pellets dried by increasing the temperature and adjusting the inlet air volume for about 10 to about 30 minutes. The pellets are removed from the chamber and sifted to collect the 12/20 fraction, which is dried in a hot-air oven at about 70° C. for about 15 to about 24 hours. The dried 12/20 fraction of pellets is reintroduced into the rotor granulator and the temperature, the rotor speed and the inlet air-volume adjusted to produce a fluidized ring. An alcoholic solution in which each 100 g of solution contained 7 g of ethyl cellulose and 0.8 g of propylene glycol is sprayed into the fluidized ring until the ethyl cellulose content of the coated particles reaches about 0.4 by weight. After the spraying is completed, the temperature of the inlet air is increased to about 50° C. while the rotation is continued for about 5 to 10 minutes.

EXAMPLE 2

A preferred high assay theophylline-containing composition is prepared utilizing the following ingredients in the amounts indicated below.

| Ingredient | Amount per 100 g |
| --- | --- |
| theophylline USP (micronized anhydrous powder) | 60 g |
| theophylline USP anhydrous (25/30 mesh fraction) | 24 g |
| pharmaceutical glaze (four pound cut) | 46 g |
| (total shellac solids content) | (16 g) |
| ethyl cellulose 10 cps | 0.4 g |
| propylene glycol USP | 0.04 g |
| denatured ethanol | qs |

The micronized theophylline anhydrous powder is dispersed in about 46 g of pharmaceutical glaze and about 42 g of denatured ethanol in a mixer or homogenizer. A Glatt Rotor Granulator (Model RGR-5) fitted with a Glatt GPCG 5/9 coating device and having parts like those shown in the apparatus of FIG. 1 is used to coat 24 g of the theophylline 25/30 mesh powder, which are charged into the chamber 1. The rotor speed is set and maintained at 150 rpm, the air pressure is set at 1,100 m³ per hour, the temperature of the inlet air volume is set at about 40° C., and the fluidized ring temperature is set at about 30° C. The slurry of theophylline is sprayed into the fluidized ring through two nozzles at an increasing rate, which varies within the range of about 50 to about 500 g/min. After all of the slurry is sprayed, rotation is continued and the theophylline-shellac pellets dried by increasing the temperature and adjusting the inlet air volume for about 10 to about 30 minutes. The pellets are removed from the chamber and sifted to collect the 12/20 fraction, which is dried in a hot-air oven at about 70° C. for about 15 to about 24 hours. The dried 12/20 fraction of pellets is reintroduced into the rotor granulator and the temperature, the rotor speed and the inlet air-volume adjusted to produce a fluidized ring. An alcoholic solution in which each 100 g of solution contains 7 g of ethyl cellulose and 0.8 g of propylene glycol is sprayed into the fluidized ring until the ethyl cellulose content of the coated particles reaches about 0.4% by weight. After the spraying is completed, the temperature of the inlet air is increased to about 50° C. while the rotation is continued for about 5 to 10 minutes.

EXAMPLE 3

The pellets prepared according to Example 2 above are maintained in the rotor granulator for about 5 minutes after the last described spraying step has been completed at which time a n alcoholic solution containing ethyl cellulose (2.4 g), pharmaceutical glaze (13.8 g) in each 100 g of denatured alcohol is sprayed into the mixing chamber until the solids content of the outermost coating reaches 0.15% by weight. Upon completion of the spraying operation, the temperature of the inlet air is increased to about 50° C. and rotation continued for about 5 to 10 minutes.

The coated pellets prepared according to Examples 1, 2 or 3 may be encapsulated or formed into tablets.

The dissolution characteristics of the pellets prepared according to the present process have been determined in the laboratory using a dissolution apparatus equipped to measure the concentration of dissolved pharmaceutical material as a function of time and as a function of the pH of surrounding fluids. The time-dependant, pH-constant, dissolution characteristics of the theophylline-containing compositions prepared in accordance with the process described in Examples 1 and 2 above and containing about 0.4 w/w % ethyl cellulose in the porous membrane layer are presented in Table 1 below. Table 2 below presents the time- and pH-dependant dissolution characteristics of the theophylline pellets prepared according to Example 1 above. The data presented in the tables below is expressed as a percent of the theophylline dissolved in the pellets and demonstrates the steady release of theophylline from the composition to provide a nonfluctuating supply of theophylline over a period of time to the blood stream of a patient.

Table 1

| | Dissolution[a] of Theophylline Pellets at Constant pH | | |
|---|---|---|---|
| | Example 1 | | |
| Hours | Lot 1 | Lot 2 | Example 2 |
| 1 | 18 | 16 | 24 |
| 2 | 32 | 30 | |
| 3.5 | 51 | 49 | 59 |
| 5 | 63 | 61 | 73 |
| 7 | 75 | 74 | 87 |
| 10 | 87 | 87 | 96 |
| 14 | 94 | 94 | |
| 24 | 98 | 98 | |

[a]The apparatus paddles are set at 50 rpm. The solution in which six capsules of the composition are dissolved comprises initially 900 ml of a pH 3 buffer, which is changed to pH 7.4 after 3.5 hours by the addition of sodium hydroxide.

TABLE 2

| | Dissolution of Theophylline Pellets as a Function of pH | | | | | | | | | |
|---|---|---|---|---|---|---|---|---|---|---|
| Hours | pH 1.22[a] | | pH 2.91 | | pH 5.56[b] | | pH 6.54[b] | | pH 7.56[b] | |
| 1 | 23 | 25 | 17 | 19 | 16 | 19 | 17 | 17 | 21 | 23 |
| 3.5 | 51 | 55 | 50 | 52 | 45 | 49 | 47 | 49 | 59 | 64 |
| 5 | 62 | 67 | 58 | 61 | 56 | 60 | 58 | 60 | 69 | 73 |
| 7 | 71 | 76 | 67 | 69 | 66 | 67 | 68 | 69 | 78 | 82 |
| 10 | 83 | 87 | 79 | 81 | 78 | 80 | 80 | 80 | 89 | 92 |

[a]dissolution medium comprises 0.1 N HCl.
[b]dissolution medium comprises 0.05M sodium acetate and 0.05M monobasic potassium phosphate, which is adjusted to the stated pH by the addition of HCl or NaOH.

The controlled release and bioavailability characteristics of the preferred theophylline-containing compositions of the present invention enable the asthma patient to ingest a predetermined dosage amount about once or twice a day and to thereby maintain a therapeutic level of active ingredient in the bloodstream. Furthermore, the present invention can be formulated to provide a controlled release composition which maintains a relatively invariant steady state concentration of active ingredient in the blood. Fluctuations in blood levels of the active ingredient are reduced, and accordingly, the therapeutic effect increased and side effects lessened.

The composition aspect of the present invention relates to a sustained release composition in which the pharmacologically active material such as theophylline is contained in a single coating of a multi-coated pellet and which provides a sustained release thereof over a period of about 12 hours. A special embodiment of the composition aspect of this invention is a higher assay composition wherein the pharmaceutically active material also comprises the seed core of the pellet. A preferred embodiment of the composition aspect of the present invention comprises a theophylline-containing pharmaceutical composition which is particularly suitable for the treatment of individuals suffering from bronchial disorders such as asthma in that it provides a means for maintaining a therapeutically effective amount of theophylline in the bloodstream over extended periods of time, for example, up to 12 hours regardless of the timing or frequency of food intake. This preferred embodiment comprises a composition prepared according to the process described above including an outermost non-enteric coating.

We claim:

1. A process for the preparation of a sustained release pharmaceutical composition, including a seed particle coated with a pharmacologically active compound-containing layer, comprising
   (A) forming a fluidized ring of said seed particles by subjecting simultaneously said particles to a centrifugal force, a perpendicular gravitational force, and a circumferential positive fluid pressure force substantially opposed to said gravitational force; and
   (B) contacting said particles while they are maintained suspended in said ring with a liquid composition containing said pharmacologically active compound and an alkali soluble material and for a period of time sufficient to coat said particles.

2. A process according to claim 1, wherein said fluidized ring of seed particles is charged with a suspension of pharmacologically active particles and an alkali soluble material in a dispersant comprising a lower alkyl alcohol.

3. A process according to claim 2, wherein said fluid utilized to form said fluidized ring comprises an inert gas.

4. A process according to claim 3, wherein said inert gas is maintained at a temperature sufficient to volatilize said dispersant.

5. A process according to claim 4, wherein the temperature of said gas is about 30° to about 75° C.

6. A process according to claim 5, wherein said suspension of pharmacologically active compound and alkali soluble material is sprayed into said fluidized ring of seed particles.

7. A process according to claim 6, wherein said diluent is substantially volatilized forming a coated particle.

8. A process according to claim 7, wherein a porous membrane is formed on said coated particles by
   (C) contacting said coated seed particles while they are maintained and suspended in a fluidized ring with a porous membrane-forming solution comprising a mixture of an alkali insoluble and acid insoluble component and a water soluble component.

9. A process according to claim 8, wherein said porous membrane-forming solution comprises a lower alkylene glycol and a lower alkyl cellulose ether material.

10. A process according to claim 9, wherein said pharmacologically active compound comprises theophylline or a derivative thereof.

11. A process according to claim 10, wherein said alkali soluble material comprises shellac.

12. A process according to claim 11, wherein said seed particles have a mean particle size of about 600 to about 725 microns.

13. A process for the preparation of a sustained release theophylline composition comprising
   (A) forming a fluidized ring of seed particles by simultaneously subjecting said particles to a centrifugal force, a gravitational force perpendicular thereto and a circumferential positive fluid pressure substantially opposed to said gravitational force;
   (B) charging said ring with an alcoholic suspension of theophylline particles and shellac and maintaining said seed particles in suspension in said ring in contact with said suspension for a period of time sufficient to form theophylline coated core particles; and (C) contacting said coated core particles while they are maintained and suspended in a fluidized ring with a solution comprising a mixture of an alkali insoluble and acid insoluble component and a water soluble component.

14. A process according to claim 13, wherein said suspension of theophylline comprises about 52 to about 65 wt. % of pharmaceutical glaze comprising about 14 to about 17 wt. % of shellac in a lower alkyl alcohol, and theophylline powder having a mean particle size of about one to about 20 microns.

15. A process according to claim 14, wherein said coated core particle is coated with an alcoholic solution of a lower alkyl glycol and a lower alkyl cellulose ether material.

16. A sustained release composition prepared according to claim 1.

17. A sustained release composition prepared according to the process of claim 8 including a seed particle core, a single layer containing a pharmacologically active material and a porous membrane-forming coating comprising a mixture of an alkali insoluble and acid insoluble component and a water soluble component.

18. A sustained release composition prepared according to the process of claim 3 including an outermost coating formed from a mixture of materials, one of which is both acid insoluble and alkali insoluble and the other material is alkali soluble and acid insoluble.

19. A composition according to claim 16 wherein said pharmacologically active material is theophylline or its derivatives.

20. A composition according to claim 16 wherein said seed particle comprises pharmaceutically active material.

21. A method for the treatment of bronchial disorders in a patient suffering therefrom including maintaining a therapeutically effective and substantially non-fluctuating amount of theophylline in said patient's bloodstream regardless of the timing or frequency of food intake comprising administering to said patient about two times daily a therapeutically effective dosage amount of a composition prepared according to claim 19.

22. A process according to claim 1, wherein said particles are compatible with said active compound and have a mean particle size of about 600 to about 850 microns.

23. A process according to claim 22, wherein said particles are contacted in a single coating application with said liquid composition.

24. A process according to claim 23, wherein said liquid composition contains from about 40 to about 55 wt. % of said active compound.

* * * * *